United States Patent [19]

Denecker et al.

[11] Patent Number: 4,762,931

[45] Date of Patent: Aug. 9, 1988

[54] PROCESS FOR THE WORK-UP OF THE MOTHER LIQUORS FROM THE PREPARATION OF BENZOTHIAZOLE COMPOUNDS

[75] Inventors: Gabriel Denecker, Kalmthout; Domien Sluyts, Stabroek, both of Belgium; Jean-Marie Biot, Rio de Janiero, Brazil; Tony van Osselaer, Belsele; Jan de Roos, Beveren, both of Belgium; Pol Bamelis, Bergisch Gladbach, Fed. Rep. of Germany

[73] Assignee: Bayer Aktiengesellschaft, Leverkusen-Bayerwerk, Fed. Rep. of Germany

[21] Appl. No.: 934,329

[22] Filed: Nov. 24, 1986

[30] Foreign Application Priority Data

Dec. 4, 1985 [DE] Fed. Rep. of Germany ....... 3542795
Jun. 21, 1986 [DE] Fed. Rep. of Germany ....... 3620822

[51] Int. Cl.$^4$ ............................................. C07D 277/36
[52] U.S. Cl. ................................... 548/166; 548/167; 548/168

[58] Field of Search ............... 548/167, 165, 176, 182, 548/189, 168, 160

[56] References Cited

U.S. PATENT DOCUMENTS

| | | | |
|---|---|---|---|
| 2,268,467 | 12/1941 | Ashworth | 548/168 |
| 2,809,202 | 10/1957 | Schoene et al. | 548/168 |
| 2,875,208 | 2/1959 | D'Amico | 548/168 |
| 2,930,794 | 3/1960 | Lober et al. | 548/168 |

Primary Examiner—Robert Gerstl
Attorney, Agent, or Firm—Connolly and Hutz

[57] ABSTRACT

An improved work-up of aqueous mother liquors which originate from the oxidative preparation of benzothiazolylsulphenamides and which contain unreacted amine or a low-boiling alcohol employed as solubilizer, or both, the work-up being carried out in such a fashion that the mother liquor is saturated by additives until two phases form, the phases are separated from one another, the aqueous phase is extracted with further alcohol or amine, amine, alcohol and the extracted components are isolated from the combined organic phases, and amine or alcohol dissolved in the aqueous phase is removed therefrom by distillation.

3 Claims, No Drawings

PROCESS FOR THE WORK-UP OF THE MOTHER LIQUORS FROM THE PREPARATION OF BENZOTHIAZOLE COMPOUNDS

The invention relates to a process for the work-up of aqueous mother liquors which originate from the oxidative preparation of compounds of the formula

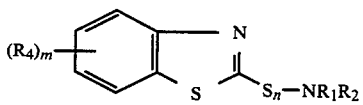

in which
m denotes 0, 1 or 2,
n denotes 1 or 2,
$R_1$ denotes hydrogen, $C_1$-to $C_6$-alkyl or $C_5$-to $C_8$-cycloalkyl,
$R_2$ denotes $C_1$-to $C_6$-alkyl or $C_5$-to $C_8$-cycloalkyl, or
$R_1$ and $R_2$ together denote $-(CH_2)_5-$ or

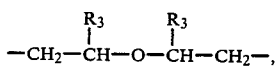

and
$R_3$ denotes $C_1$-$C_6$-alkyl and/or hydrogen, and
$R_4$ denotes hydrogen or $C_1$-$C_6$-alkyl,
from optionally nuclear-substituted 2-benzothiazolyl disulphides, 2-mercaptobenzothiazoles or 2-mercaptobenzothiazole salts and the appropriate amines and, if appropriate, sulphur, and contain unreacted amine or low-boiling alcohol employed as solubilizing agent, or both.

Such mother liquors are produced during the preparation of compounds which are used as vulcanization accelerators. Examples are:
Benzothiazolyl-2-cyclohexylsulphenamide, benzothiazolyl-2-tert.butylsulphenamide, benzothiazolyl-2-sulphenmorpholide, benzothiazolyl-2-diethylsulphenamide, benzothiazolyl-2-diisopropylsulphenamide, benzothiazolyl-2-dicyclohexylsulphenamide and 2-(4-morpholinyldithio)-benzothiazole.

These mother liquors furthermore contain non-negligible concentrations of by-products which contain sulphur and/or nitrogen. The mother liquors are conventionally worked up by distillative recovery of the organic solvent or of the amine. During this procedure, water-insoluble organic by-products which are not readily volatile separate out in the form of resinous flakes or tar. These lead to contamination and blockage of the distillation apparatus and of the downstream parts of the plant and necessitate time-consuming and expensive cleaning operations. The remaining, water-soluble organic by-products, for example benzothiazole-2-sulphinic acid and benzothiazole-2-sulphonic acid and their salts remain in the waste-water thus treated in dissolved form. Since an economic method for the elimination of these products from the waste-water is not known hitherto, the only possibility is to burn the residues after partial or complete evaporation. The work-up of the mother liquors of the process mentioned is thus not only afflicted with chemical engineering problems, but is also very energy-intensive.

The invention has the object of providing a work-up process using which the organic components can be removed from the mother liquor, contamination or blockage by resins and tar do not occur, and waste-water remains which can be discharged into the environment without having to be evaporated and burnt.

The object is achieved according to the invention in that the mother liquor is saturated with additives until two phases form, the phases are separated from one another, the aqueous phase is extracted with further alcohol or amine, the extraction agent and the extracted components are isolated from the combined organic phases, and amine or alcohol dissolved in the aqueous phase are removed therefrom by distillation.

The extracted organic and inorganic components in the organic phase are obtained, after removal of the readily volatile alcohols and amines by distillation, in the form of a melt, which, because of the high ash content, cannot be utilized without demineralization. Therefore, in a further embodiment of the process according to the invention, the organic phase is initially only concentrated, during the distillative recovery of the extraction agent, until the residue separates into two liquid phases, on the one hand a low-salt concentrate of extracted benzothiazole derivatives in the form of a melt and on the other hand an aqueous solution of the co-extracted inorganic salts. By separation of the two phases, organic and inorganic products can easily be separated from one another and worked up separately.

The melt can be worked up to give usable substances or can be burnt to utilize its energy content. The aqueous solution can be transferred into an earlier process stage, if appropriate after stirring with amine or alcohol.

If the mother liquor to be worked up contains non-negligible residual concentrations of N-chloramines, then it is expedient to destroy these in a conventional manner by addition of reducing agents before the actual work-up.

For the saturation of the mother liquor to be worked up, there are several procedures, which must at all events be designed so that simultaneous precipitation of resinous flakes or tar does not occur in spite of the saturation.

Thus, the aqueous mother liquor of the synthesis reaction can be mixed with an amount of alcohol or amine which is adequate for this purpose. This procedure usually requires relatively large amounts of alcohol or amine.

A salt, particularly an inorganic sodium salt, is used expediently, sodium sulphate or sodium chloride, or mixtures of these two salts, being used particularly. The sodium salt is preferably produced first in the mother liquor, for example by simultaneous or successive addition of sulphuric acid, or hydrochloric acid, or mixtures of the two acids, and sodium hydroxide solution. In particular, concentrated acids and concentrated sodium hydroxide solution are employed here so that the amount of mother liquor is not increased unnecessarily. The use of concentrated sulphuric acid or hydrochloric acid at a pH below 2, preferably below 1, and holding the mixture at this pH for 3 minutes to 20 hours, preferably 30 minutes to 2 hours, at 20° to 250° C., preferably 60° to 120° C., additionally has the advantage that polar benzothiazole compounds in the mother liquor are converted to less polar compounds which are thus taken up in the organic phase more easily. A pH of 1 to 11, preferably 4 to 10, is then set using sodium hydroxide solution.

The two-phase system can be separated in any separation apparatus which is suitable for this. There are likewise no limitations regarding the apparatus for the extraction of the aqueous phase using further alcohol and/or amine. Countercurrent columns or optionally multistage mixer/separator combinations are advantageously employed. The number of theoretical extraction stages necessary for adequate purification of the aqueous phase is about 3 to 8.

This extraction is carried out technically elegantly using a column, the saturated mother liquor being introduced onto the column and separated there. The aqueous phase flows downwards through the column, and the extraction liquid, fed into the bottom of the column, flows against the aqueous phase and combines with the organic phase from the mother liquor at the phase boundary surface at the top of the column. The combined organic phases are removed from the top and worked up by distillation. The organic phase can be concentrated without significant baking on or contamination in all evaporators which are suitable for medium viscosity liquids.

Particularly suitable for this purpose are, inter alia, falling-film evaporators, thin-film evaporators and coiled-tube evaporators. The alcohol and/or amine can also be recovered completely from the exhaust vapours of the partial concentration and from the extracted aqueous phase using conventional distillation techniques, without significant contamination of the distillation apparatus and the downstream parts of the plant occurring.

Preferably, the distillation is carried out so that the recovered extraction agent contains no more than 40% by weight of dissolved water.

0.05–1, preferably 0.1–0.5, parts by weight of extraction agent at pH 1 to 11, preferably 4 to 10, and at 60° to 120° C. are employed per part by weight of the aqueous solution to be extracted.

EXAMPLE 1

(comparison experiment)

As a comparison with the work-up of mother liquors by the process according to the invention (Examples 2 and 3), the state of the art is illustrated using the following example.

35.2 kg of a mother liquor comprising 23.2% by weight of isopropanol, 0.86% by weight of organic carbon (excluding isopropanol), 11.5% by weight of $NaCl + Na_2SO_4$, and the remainder of water, from the preparation of benzothiazolyl-2-dicyclohexylsulphenamide are distilled together with 12 kg of wash-water from the filtration stage (31.7% by weight in isopropanol) for recovery of the isopropanol.

The water-insoluble components of the mother liquor employed separate off during this in the form of a tarry, viscous liquid, with the result that the distillation column and the downstream parts of the plant have to be cleaned very frequently. 33.2 kg of heavily contaminated waste-water are obtained as an aqueous bottom phase from which only a fraction of the organic carbon pollutants can be removed by stirring with relatively large amounts of activated charcoal:

|  | without post-treatment | post-treatment with 10 g of activated charcoal per l |
|---|---|---|
| Org. carbon (% by weight) | 0.46 | 0.24 |
| CSB (mg 0/l) | 13,000 | 8,300 |

EXAMPLE 2

35.2 kg of a mother liquor comprising 22.8% by weight of isopropanol, 0.98% by weight of organic carbon (excluding isopropanol), 9.4% by weight of $NaCl + Na_2SO_4$, and the remainder of water, from the preparation of benzothiazole-2-dicyclohexylsulphenamide (discharge from filtration unit; without wash-water), are adjusted to pH 0.5–0.8 using concentrated sulphuric acid, stirred for one hour at 80° C., and adjusted to pH 7 to 8 using concentrated sodium hydroxide solution with addition of a mixture of 3.3 kg of aqueous salt solution from the partial concentration and 1 kg of isopropanol distillate.

The two-phase mixture which forms during this operation is subsequently brought into contact with a countercurrent of 4.8 kg of isopropanol distillate in a packed column at 70° C. 23.5 kg of extracted aqueous solution I and 24.4 kg of extract phase II are obtained which have the following analyses:

|  | Aqueous phase I | Organic phase II |
|---|---|---|
| isopropanol | 7.5% by weight | 46.2% by weight |
| organic carbon (excluding isopropanol) | 0.095% by weight | 1.57% by weight |

The yield of the extractive purification is thus 94%.

640 g of a tarry melt are isolated, besides 3.3 kg of an aqueous salt solution, by partial concentration of isopropanolic phase II with subsequent warm separation of the two-phase liquid residue, the salt solution being fed back to the neutralization stage for further purification.

Finally, 16.6 kg of aqueous isopropanol (azeotropic mixture) are recovered as distillate from the exhaust vapours of the partial concentration and from the extracted aqueous phase I and from the diluted washwater from the filtration stage. The waste-water resulting from this process is clear as water and free of grease, and is discharged without contamination to the distillation apparatus and the downstream piping.

EXAMPLE 3

Sodium sulphite is added at 60° C. to 20.2 kg of a mixture of mother liquor and wash-waters containing 3.0% by weight of diisopropylamine (DIPA) and 0.3% by weight of organic carbon (excluding DIPA) from the synthesis of benzothiazolyl-3-diisopropylsulphenamide, 470 g of a DIPA-rich phase I separating off. The aqueous solution obtained during this is adjusted to pH 0.5 using concentrated sulphuric acid, stirred for about one hour at 75° C. and subsequently adjusted to pH 8.0 using concentrated sodium hydroxide solution so that it can then be extracted with 5.4 kg of 91% strength DIPA in a packed column at 60° C. On the one hand, 23.6 kg of extracted aqueous phase II and, on the other hand, 4.75 kg of a DIPA-rich extract III are produced.

The combined organic phases I and III, after addition of 260 g of water, are partially concentrated in order to separate off the extracted components, a two-phase mixture being produced which can be divided by warm phase separation into, on the one hand, 80 g of a virtually salt-free tarry melt and, on the other hand, 90 g of an aqueous solution.

Finally, the diisopropylamine is recovered in an azeotropic concentration from the exhaust vapours of the partial concentration and from the extracted aqueous phase II by distillation, 24 kg of water-clear and grease-free waste-water containing 0.038% by weight of organic carbon (CSB: 1630 mg 0/1) being obtained.

The overall yield of the purification procedure is 85%.

We claim:

1. Process for the work-up of aqueous mother liquors comprising at least one member selected from the group consisting of benzothiazole-2-sulphinic acid, benzothiazole-2-sulphonic acid and their salts as by-products which originate from the oxidative prepration of compounds of the formula

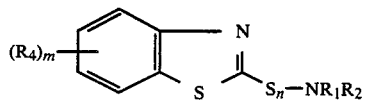

in which m denotes 0,1 or 2, n denotes 1 or 2, $R_1$ denotes hydrogen, $C_1$- to $C_6$-alkyl or $C_5$- to $C_8$-cycloalkyl, $R_2$ denotes $C_1$- to $C_6$-alkyl or $C_5$- to $C_8$-cycloalkyl, or $R_1$ and $R_2$ together denote —$(CH_2)_5$— or

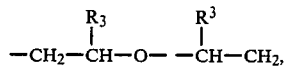

and $R_3$ denotes $C_1$-$C_6$-alkyl or hydrogen, and $R_4$ denotes hydrogen or $C_1$-$C_6$-alkyl, from optionally nuclear-substituted 2-benzothiazolyl disulphides, 2-mercaptobenzothiazoles or 2-mercaptobenzothiazole salts and the corresponding amines and, if appropriate, sulphur, and contain unreacted amine or a low-boiling alcohol employed as solubilizer, or both, characterized in that the mother liquor is saturated by sodium sulphate, sodium chloride or both in such a fashion that the pH is adjusted to below 2 by the addition of concentrated sulphuric acid, hydrochloric acid or both are added, the mixture is subsequently kept at 20° to 250° C. for 3 minutes to 20 hours and then the pH is adjusted to 4 to 10 by the addition of a concentrated sodium hydroxide solution where upon two phases form, the phases are separated from one another, the aqueous phase is extracted with further alcohol or amine, the extraction agent and the extracted components are isolated from the combined organic phases, and amine or alcohol dissolved in the aqueous phase is removed therefrom by distillation.

2. Process according to claim 1, characterized in that the combined organic phases, in order to recover the extraction agent, are only concentrated until the residue separates into two liquid phases, on the one hand a low-salt concentrate of extracted benzothiazole derivatives in the form of a melt and, on the other hand, an aqueous solution of the co-extracted inorganic salts, and the two phases are separated from one another and worked up separately.

3. Process according to claim 1, characterized in that the extraction is carried out at 60° to 120° C.

* * * * *